(12) United States Patent
Wepfer

(10) Patent No.: US 7,273,887 B1
(45) Date of Patent: Sep. 25, 2007

(54) TOPICAL ANESTHETIC FORMULATION

(75) Inventor: Scott Wepfer, Hoover, AL (US)

(73) Assignee: Transdermatech, Inc., Tuscaloosa, AL (US)

( * ) Notice: Subject to any disclaimer, the term of this patent is extended or adjusted under 35 U.S.C. 154(b) by 31 days.

(21) Appl. No.: 10/111,241

(22) PCT Filed: Oct. 23, 2000

(86) PCT No.: PCT/US00/41451

§ 371 (c)(1),
(2), (4) Date: Jul. 10, 2002

(87) PCT Pub. No.: WO01/41550

PCT Pub. Date: Jun. 14, 2001

Related U.S. Application Data

(60) Provisional application No. 60/161,155, filed on Oct. 22, 1999.

(51) Int. Cl.
*A61K 31/24* (2006.01)
*A61K 31/16* (2006.01)
*A61K 9/07* (2006.01)

(52) U.S. Cl. ............... 514/535; 514/536; 514/537; 514/626; 424/449

(58) Field of Classification Search ............. 514/622, 514/535, 536, 537, 626; 424/449
See application file for complete search history.

(56) References Cited

U.S. PATENT DOCUMENTS

| | | | |
|---|---|---|---|
| 3,832,460 A | 8/1974 | Kosti | 424/54 |
| 4,808,410 A | 2/1989 | Sorrentino et al. | 424/435 |
| 5,534,242 A * | 7/1996 | Henry | 424/45 |
| 5,585,398 A * | 12/1996 | Ernst | 514/537 |
| 5,900,249 A | 5/1999 | Smith | 424/443 |
| 6,295,469 B1 * | 9/2001 | Linkwitz et al. | 604/20 |
| 6,528,086 B2 * | 3/2003 | Zhang | 424/449 |

OTHER PUBLICATIONS

Remington's Pharmaceutical Sciences, 17th Edition, 1985. p. 17920.*

Williams et al. Benzyl Alcohol Attenuates the Pain of Lidocaine Injections and Prolongs Anesthesia. J. Dermatol Surg Oncol. 1994 vol. 20, pp. 730-733.*

Vaida et al. Prolongation of lidocaine spinal anesthesia with phenylephrine. Anesthesia and Analgesia, 1986, vol. 65, No. 7, pp. 781-785.*

* cited by examiner

*Primary Examiner*—Jennifer Kim
(74) *Attorney, Agent, or Firm*—Gifford, Krass, Sprinkle, Anderson & Citkowski, P.C.

(57) ABSTRACT

The topical anesthetic formulation of the present invention is typically a solution that preferably includes lidocaine, USP as the active anesthetic ingredient with benzyl alcohol and isopropyl alcohol. This invention deals with problems commonly associated with topical application of local anesthetics such as: slow onset of action; need for occlusion; messiness of creams, ointments or gels; and rapid loss of effect due to rapid systemic dispersion. The invention permits enhanced penetration of the anesthetic and thereby allows for a lesser total dosage of pharmaceutically active ingredient. The use of a lesser total dosage also decreases systemic toxicity.

11 Claims, No Drawings

TOPICAL ANESTHETIC FORMULATION

This application is a U.S. National Phase of PCT application number PCT/US00/41451 filed Oct. 23, 2000, which claims benefit of a non-provisional of U.S. application No. 60/161,155 filed Oct. 22, 1999.

FIELD OF THE INVENTION

The present invention generally relates to topical anesthetics. More particularly, the present invention relates to a fast acting topical anesthetic or transdermal pain formulation for deep dermis anesthesia for use prior to and/or during medical procedures.

BACKGROUND OF THE INVENTION

The use of topical or dermal anesthetics has long been utilized in the practice of medicine. Topical anesthetics are commonly administered prior to procedures such as injections, biopsies, the application of laser energy for cutaneous procedures such as removal of hair, tattoos, telengectasias, etc., minor superficial surgeries, and the like.

One particular topical anesthetic utilized to suppress or eliminate pain during such procedures is known by the trade name EMLA®. This product is known to be effective as a topical anesthetic; however, EMLA® has a very long onset time, which is the time between administration of the topical anesthetic and the commencement of the anesthetic effect. It must also be covered with an occlusive dressing to enhance penetration. The onset time for EMLA® can range from 45 to 90 minutes and, in some instances, can take even longer. The variability in length of onset time leads to delays in the commencement of medical procedures and, because of the very wide variation in onset time, can lead to the premature commencement of procedures, thereby inflicting unnecessary pain on the patient.

Several topical anesthetic formulations have been extensively used by the medical field to obtain local anesthesia. These products are known to be effective as topical anesthetics; however, they typically have long onset times, which is the time between the administration of the topical anesthetic and the commencement of the anesthetic effect. They must also be covered with an occlusive dressing to enhance penetration. Also, the onset of action for these available topical anesthetics varies over a range of time, for example from 45 to 90 minutes. This variability in length of onset time leads to delays in the commencement of medical procedures and, because of the very wide variation in onset time, can lead to the premature commencement of procedures, thereby inflicting unnecessary pain on the patient. These current methods have used more viscous semi-liquid carriers such as creams, ointments or gels which can be quite messy to work with, which adds another inconvenience to the user. For example, they must be cleaned off the injection site before injecting.

Accordingly, it would be advantageous and desirable to develop a topical anesthetic formulation which has a shorter onset time, which has less variability in the onset time, does not require occlusion, is easier to apply with less mess and which is amenable to use for cutaneous laser procedures such as hair removal and skin resurfacing, as well as for use before giving injections, starting IVs, drawing blood, biopsies and minor superficial surgeries. Such a formulation will have a potent clinical use with a more rapid onset of action.

The ideal vehicle for such a formulation would enhance the percutaneous penetration of the active ingredient, allowing for a fast onset of action. At the same time, the active ingredient must not penetrate so effectively through the skin as to be rapidly lost to the systemic circulatory systems. Thus, the ideal vehicle would also enhance the skin's ability to retain the pharmacologically active ingredient or, in other words, to increase skin residence times.

BRIEF SUMMARY OF THE INVENTION

The present invention concerns a topical anesthetic formulation for topical administration to the surface of the skin and into the deeper regions of the dermis. The topical anesthetic formulation of the present invention is typically a solution that preferably includes lidocaine, USP as the active anesthetic ingredient. Additional constituents illustratively include benzyl alcohol and isopropyl alcohol.

The invention confronts the paradoxical requirement that a local anesthetic quickly penetrate into the skin and produce a rapid onset of action, yet not penetrate the skin until it reaches into the systemic circulation. The anesthetic does not have an adversely prolonged effect.

The present invention permits enhanced penetration of the anesthetic and thereby allows for a lesser total dosage of pharmaceutically active ingredient. The use of a lesser total dosage also decreases systemic toxicity.

DETAILED DESCRIPTION OF THE INVENTION

The present invention provides a topical anesthetic formulation for topical administration to the surface of the skin and into the deeper regions of the dermis. The topical anesthetic formulation of the present invention is typically a solution which includes lidocaine, USP; benzyl alcohol, NF, anhydrous, isopropyl alcohol and USP.

Lidocaine, USP is the preferred active anesthetic ingredient. Advantages include its time to onset of action which is 0.5 to 1 minute. Another advantage of lidocaine is that methemoglobinemia is not a concern as it is in formulations which contain prilocaine.

The base or unionized form of this drug was intentionally chosen because it is significantly more soluble in benzyl alcohol and also because studies show that bases of local anesthetics more easily traverse the stratum corneum than do their salts. Lipid solubility appears to not only be the primary determinant of intrinsic anesthetic potency, the onset of action is also directly related to the percent of drug that exists in the base form since it is unchanged for that is primarily responsible for diffusion across the nerve sheath.

The key to this non-aqueous solvent and transdermal penetration system is benzyl alcohol. Benzyl alcohol has demonstrated its ability to not only solvate lipophilic (nonionic) compounds, but to form a micelle, a property conducive to penetration of the stratum corneum. The high lipid solubility of lidocaine base as well as that of the benzyl alcohol greatly diminishes the need for a vasoconstrictor to be added to the formula to prolong the duration of anesthesia. Thus, the lipophilic nature is seen as a positive quality since vasoconstrictors are also contraindicated for many of the procedures for which this system will benefit, such as starting an IV and laser removal of telengiectasias. In both of these instances, vasoconstriction decreases the chances for success of the medical procedure.

The amphoteric properties of benzyl alcohol—its strong lipophilicity and moderate hydrophilicity—allow it to disrupt the highly structured lipid portion of the stratum corneum, or fluidizing its lipids, thus allowing lipid soluble drugs to pass through the stratum corneum at increased rates of absorption. It is then the same strong lipophilicity when enhances penetration that also significantly enhances the retention of lipophilic drugs in the subcutaneous tissues underlying the site of application, thus increasing the duration of local action and decreasing systemic side-effects by slowing continued penetration into the systemic circulation. Thus, more anesthetic molecules are allowed to reach the nerve membrane which improves the depth and duration of anesthesia.

Besides being an anesthetic itself, its ability to fluidize membranes may also play a role in the system's ability to bring about such a markedly fast onset of action.

The isopropyl alcohol is used as a co-solvent. Once applied to the skin, this co-solvent rapidly evaporates from the skin due to its greater volatility. As this happens, the drug is transferred to the less volatile phase, benzyl alcohol, which, due to its very rapid permeation and good solvent characteristics, prevents the deposition of solutes on the skin surface.

It is appreciated that other topical anesthetic compounds are operative herein in place of the above active anesthetic. Alternative topical anesthetic compounds illustratively include bupivacaine, chloroprocaine, oxyprocaine, mepivacaine, piperocaine, tetracaine, procaine, dibucaine, benzocaine, dyclaine and salts thereof. It is also contemplated that the present invention can optionally include a vasoconstrictor. Phenylephrine is a representative vasoconstrictor which could be utilized to keep the active ingredients localized to the site to which they are applied. Other vasoconstrictors could include naphazole, tetrahydrozoline, oxymetazoline, tramazoline, and salts thereof. The addition salts of these compounds can be utilized in the formulation of the present invention. The benzyl alcohol serves as a penetration enhancer to allow deeper layers of the dermis to be anesthetized. The isopropyl alcohol serves as a co-solvent.

Typical ranges of the present invention are provided in Table I.

TABLE I

Typical Composition Ranges for Inventive Topical Anesthetic in Total Weight Percent of the Formulation

| Agent | Component | Typical Range Values | Preferred Range |
|---|---|---|---|
| Vasoconstrictor (total) | | 0.05-5 | 1-3 |
| | phenylephrine HCl | 0.05-5 | 1-3 |
| Anesthetic (total) | | 1-25 | 5-16 |
| | procaine HCl | 0-15 | 0.5-4 |
| | lidocaine HCl | 0-20 | 0.5-6 |
| | tetracaine HCl | 0-25 | 1-9 |
| Skin Penetration Enhancer (total) | | 0-35 | 5-21 |
| | benzyl alcohol | 0-35 | 1-10 |
| | propylene glycol | 0-35 | 3-14 |
| VOC and base | | 40-99 | 70-90 |

It is appreciated that a variety of skin penetration enhancers, skin compatible and anesthetic solvating VOCs and bases in addition to those detailed herein are known to one skilled in the art. Skin penetration enhancers additionally operative here in place of or in combination with those of Table I illustratively include ethoxydiglycol and those detailed in "Percutaneous Penetration Enhancers: The Fundamentals," E. W. Smith and H. I. Maibach, July 1999, pp. 1-512, which is incorporated herein by reference. Additionally, a volatile organic compound intended to enhance evaporation such as isopropyl alcohol, an ether or halocarbon is optionally omitted in instances where rapid evaporation is not desired.

In use, a therapeutically effective amount of the topical anesthetic formulation of the present invention is applied to the skin of a patient or subject prior to and/or during a medical procedure to treat the patient or subject.

The terms "patient" and "subject" mean all animals including humans. Examples of patients or subjects include humans, cows, dogs, cats, goats, sheep, and pigs.

The term "treating" includes, but is not limited to, the application of the topical anesthetic to the skin of a patient to prevent or inhibit the sensation of pain in the vicinity or region of the application of the topical anesthetic formulation.

A therapeutically effective amount is an amount of the topical anesthetic formulation of the present invention, that when administered to a patient or subject, ameliorates, eliminates and/or inhibits pain in the local region or vicinity of the application of the topical anesthetic of the present invention.

Dosage forms for topical administration of the formulation of the present invention include creams, gels, ointments and topical sprays. The active components are admixed under sterile conditions with a physiologically acceptable carrier and any preservatives, buffers, or propellants as may be required. Ophthalmic formulations, eye ointments, powders, and solutions, as well as dental formulations containing appropriate flavors and sweeteners, are also contemplated as being within the scope of this invention.

The topical anesthetic or transdermal pain formulation of the present invention can be packaged in a spray bottle or other suitable delivery device and can be applied to the surface of the skin utilizing a cotton swab, gauze pad, or other suitable applicator. A preferred formulation of the present invention can be made by combining the following ingredients:

To make 30 ml:

| | | |
|---|---|---|
| lidocaine, USP | 1.2 gm | (active ingredient) |
| benzyl alcohol | 3.0 ml | (penetration enhancer) |
| isopropyl alcohol | 8.0 ml | (to aid in quick drying by evaporation) |

Mixing instructions:

Weigh out first four ingredients.
Transfer to 100 ml beaker.
Add paraben-preserved water.
Stir until dissolved.
When dissolved, add benzyl alcohol, isopropyl alcohol and propylene glycol.
Stir until well mixed.
Dispose in sprayer bottle.

Applicants have found the formulation according to the present invention to be 100% effective in preventing any discomfort associated with the laser removal of hair using an Alexandrite Laser in twelve of twelve patients. In six of these instances, the procedure had been previously done once before utilizing EMLA® gel which was applied approximately ninety minutes prior to the initiation of the laser hair removal. In these six patients, their procedures had to be stopped prematurely due to patient discomfort. When the patients were re-lasered after pre-treating with the transdermal pain formulation of the present invention, none of these six patients reported any discomfort from the second procedure which was completed. One of the twelve patients or subjects was a male who had hair removed from his back. This is an interesting result because, of the different types of laser hair removal procedures, the removal of hair from the back is thought to be the most painful.

While the use of the transdermal pain formulation or topical anesthetic formulation of the present invention has been described for use in the laser removal of hair, Applicant contemplates other uses including use prior to laser skin resurfacing and other cutaneous laser procedures, use prior to injection or insertion of an intravenous needle such as for the initiation of an intravenous drip, use prior to other types of needle sticks such as IM injections, inoculations and blood drawing, or other suitable uses for topical or transdermal anesthesia which are well known to those skilled in the art.

In view of the teaching presented herein, other modifications and variations of the present invention will readily be apparent to those of skill in the art. The discussion and description are illustrative of some embodiments of the present invention, but are not meant to be limitations on the practice thereof. It is the following claim, including all equivalents, which defines the scope of the invention.

The invention claimed is:

1. A formulation consisting of: at least one anesthetic compound selected from the group consisting of procaine, lidocaine, tetracaine and salts thereof; and skin penetration enhancer in an anhydrous solution, and a volatile co-solvent.

2. The formulation of claim 1 wherein said skin penetration enhancer is at least one compound selected from the group consisting of: benzyl alcohol, propylene glycol, and ethoxydiglycol.

3. The formulation of claim 1 wherein the volatile co-solvent is selected from the group consisting of isopropyl alcohol, ether and halocarbon.

4. The formulation of claim 1 wherein said at least one anesthetic compound is present in said formulation from 1 to 25 total weight percent.

5. The formulation of claim 4 wherein at least two anesthetic compounds are present in said formulation from 5 to 16 total weight percent.

6. The formulation of claim 1 wherein at least two anesthetic compounds are procaine, lidocaine and tetracaine, or salts thereof.

7. The formulation of claim 6 wherein procaine is present from 0.5-4 total weight percent, lidocaine is present from 0.5-6 total weight percent, and tetracaine is present from 1-9 total weight percent.

8. The formulation of claim 1 wherein said skin penetration enhancer is present up to 35 total weight percent.

9. The formulation of claim 8 wherein said skin penetration enhancer is present from 5 to 21 total weight percent.

10. A formulation consisting of: at least one anesthetic compound selected from the group consisting of procaine, lidocaine, tetracaine and salts thereof; an anhydrous skin penetration enhancer; a volatile co-solvent; and a vasoconstrictor present from 0.05 to 5 total weight percent.

11. A method for reducing pain associated with the application of laser energy to the skin, said method comprising the step of applying a therapeutically effective amount of the formulation according to claim 1 to the area of the skin to be treated prior to the application of laser energy.

* * * * *